US011849695B2

(12) United States Patent
Kudithipudi et al.

(10) Patent No.: US 11,849,695 B2
(45) Date of Patent: *Dec. 26, 2023

(54) DEVELOPMENT OF TOBACCO VARIETIES WITH NO OR SIGNIFICANTLY REDUCED ANATABINE CONTENT

(71) Applicant: Altria Client Services LLC, Richmond, VA (US)

(72) Inventors: Chengalrayan Kudithipudi, Midlothian, VA (US); Rutger Van Der Hoeven, Midlothian, VA (US); Ndjido Ardo Kane, Richmond, VA (US)

(73) Assignee: Altria Client Services LLC, Richmond, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/954,654

(22) Filed: Sep. 28, 2022

(65) Prior Publication Data

US 2023/0024503 A1  Jan. 26, 2023

Related U.S. Application Data

(63) Continuation of application No. 16/529,307, filed on Aug. 1, 2019, now Pat. No. 11,484,002, which is a continuation of application No. 14/207,082, filed on Mar. 12, 2014, now Pat. No. 10,375,910.

(60) Provisional application No. 61/799,831, filed on Mar. 15, 2013.

(51) Int. Cl.
*A01H 6/82* (2018.01)
*A01H 5/12* (2018.01)
*A24B 13/00* (2006.01)
*A24D 1/00* (2020.01)
*A01H 1/06* (2006.01)

(52) U.S. Cl.
CPC .............. *A01H 6/823* (2018.05); *A01H 1/06* (2013.01); *A01H 5/12* (2013.01); *A24B 13/00* (2013.01); *A24D 1/00* (2013.01)

(58) Field of Classification Search
None
See application file for complete search history.

(56) References Cited

U.S. PATENT DOCUMENTS

| | | |
|---|---|---|
| 6,135,121 A | 10/2000 | Williams |
| 6,586,661 B1 | 7/2003 | Conkling et al. |
| 6,730,832 B1 | 5/2004 | Dominguez et al. |
| 6,907,887 B2 | 6/2005 | Conklin |
| 9,096,864 B2 | 8/2015 | Lewis et al. |
| 10,375,910 B2 | 8/2019 | Kudithipudi et al. |
| 2006/0060211 A1* | 3/2006 | Conkling ............ C12N 9/1077 131/364 |
| 2007/0034220 A1 | 2/2007 | Pandolfino |
| 2007/0240728 A1 | 10/2007 | Hashimoto et al. |
| 2008/0202541 A1 | 8/2008 | Dewey et al. |
| 2008/0292735 A1 | 11/2008 | Hashimoto et al. |
| 2009/0205072 A1 | 8/2009 | Dewey et al. |

FOREIGN PATENT DOCUMENTS

| | | |
|---|---|---|
| WO | WO 2006/109197 A2 | 10/2006 |
| WO | WO 2009/064771 A2 | 5/2009 |
| WO | WO 2011/088180 A1 | 7/2011 |

OTHER PUBLICATIONS

Chintapakorn et al., "Antisense-mediated down-regulation of putrescine N-methyltransferase activity in transgenic Nicotiana tabacum L. can lead to elevated levels of anatabine at the expense of nicotine," *Plant Molecular Biology* 53(1-2), pp. 87-105 (Oct. 2003) (Dordrecht, Netherlands).

Dewey et al., "Molecular genetics of alkaloid biosynthesis in Nicotiana tabacum." *Phytochemistry* 94, pp. 10-27 (Oct. 2013) (Oxford, England, UK).

Häkkinen et al., "Anatalline and Other Methyl Jasmonate-Inducible Nicotine Alkaloids From Nicotiana Tabacum cv. BY-2 Cell Cultures," *Planta Med.* 70(10), pp. 936-941 (2004) (Stuttgart, Germany).

International Search Report dated Jul. 3, 2014, in International Application No. PCT/US2014/025871.

Julio et al., "Reducing the content of nornicotine in tobacco via targeted mutation breeding," *Molecular Breeding* 21, pp. 369-381 (Apr. 2008) (Baden-Wuerttemberg, Germany).

Lewis et al., "Transgenic and mutation-based suppression of a berberine bridge enzyme-like (BBL) gene family reduces alkaloid content in field-grown tobacco." *PloS One* 10.2, e0117273 (Feb. 2015) (electronic publication).

Sun et al., "Effects of different environmental locations on alkaloid accumulation in tobacco leaves in China," *J. Food Agric. Environ* 11, pp. 1337-1342 (2013).

Sun et al., "Genetic variation in alkaloid accumulation in leaves of Nicotiana." *Journal of Zhejiang University Science B* 14(12), pp. 1100-1109 (Dec.2013) (Baden-Wuerttemberg, Germany).

Valleau, "Breeding tobacco for disease resistance." *Economic Botany* 6.1, 69-102 (Jan. 1952) (Baden-Wuerttemberg, Germany).

* cited by examiner

*Primary Examiner* — Weihua Fan
(74) *Attorney, Agent, or Firm* — Arnold & Porter Kaye Scholer LLP

(57) ABSTRACT

A process for producing a reduced tobacco-specific nitrosamine (TSNA) tobacco plant comprising reducing and/or eliminating anatabine biosynthesis in wild-type tobacco plant. In addition, use of such plants for discovery of molecular markers that are closely linked with genes required for anatabine biosynthesis and for discovery of genes required for anatabine biosynthesis. In addition, a smoking composition, a smoking article and a smokeless tobacco oral delivery product contain the tobacco material.

16 Claims, 5 Drawing Sheets

Figure 2: Screening of EMS mutants by HPTLC method

Figure 3
(A)
M2 Generation
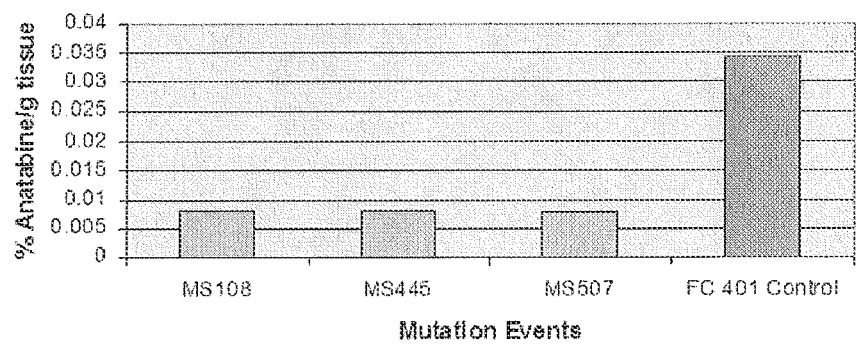
(B)
M3 Generation
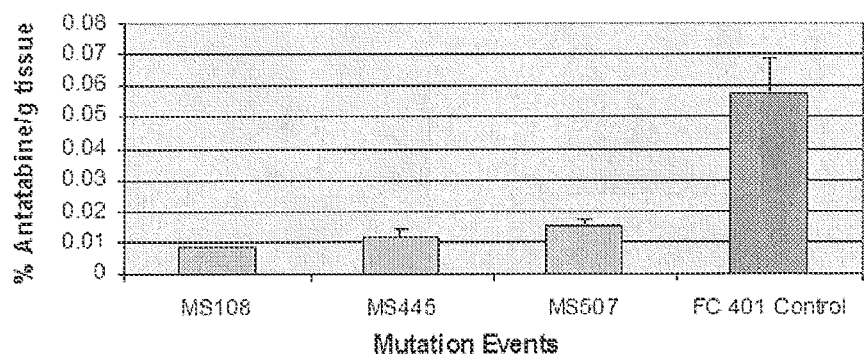
(C)
M4 Generation
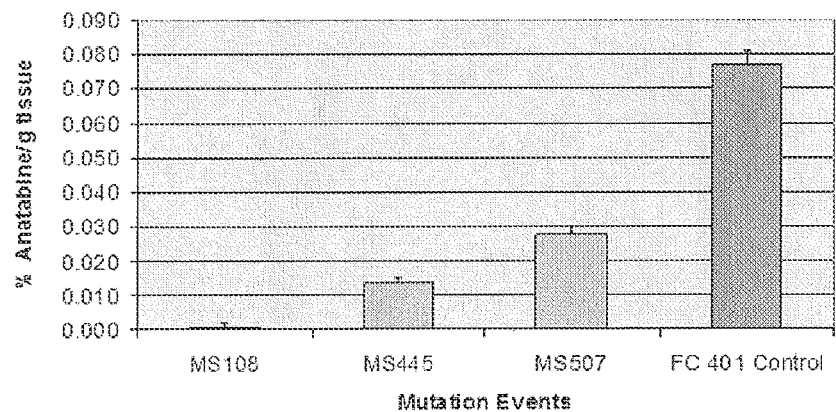

Figure 4
(A)
M2 Generation
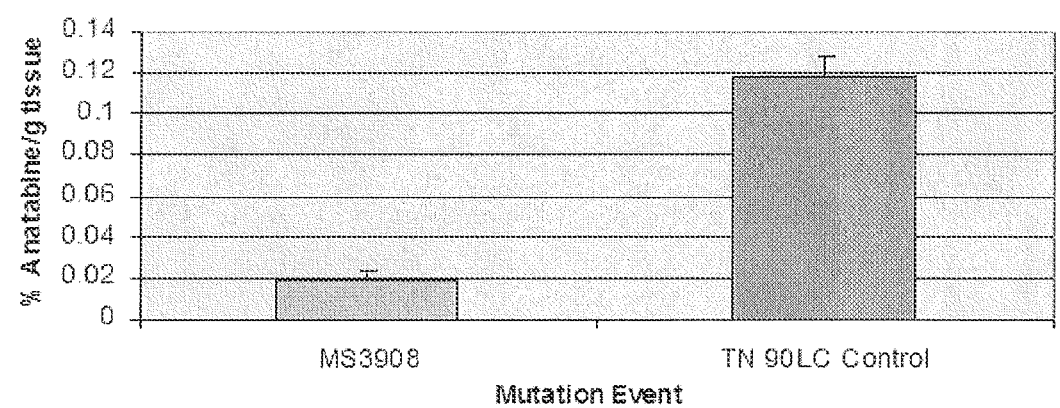
(B)
M3 Generation
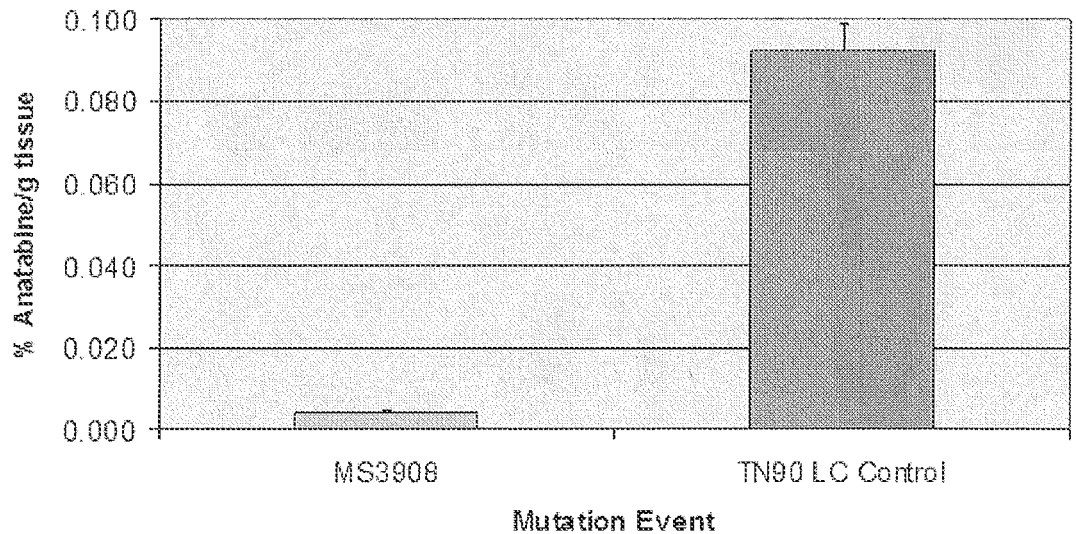

DEVELOPMENT OF TOBACCO VARIETIES WITH NO OR SIGNIFICANTLY REDUCED ANATABINE CONTENT

CROSS-REFERENCE TO RELATED APPLICATIONS

This application is a Continuation of U.S. patent application Ser. No. 16/529,307, filed Aug. 1, 2019, which is a Continuation of U.S. patent application Ser. No. 14/207,082, filed on Mar. 12, 2014 (now U.S. Pat. No. 10,375,910, issued Aug. 13, 2019), which claims the benefit of U.S. Provisional patent application Ser. No. 61/799,831, filed on Mar. 15, 2013. All three applications are incorporated herein by reference in their entireties for all purposes.

BACKGROUND

*Nicotiana tabacum* produces several different pyridine alkaloids, with nicotine representing the most abundant. The alkaloids that accumulate to a lesser degree include anatabine, nornicotine, myosmine, and anabasine. These alkaloids are commonly referred to as minor alkaloids. Minor alkaloids are direct precursors in the formation of tobacco specific nitrosamines.

Nitrosamines and in particular, tobacco specific nitrosamines (TSNAs) are constituents of tobacco. Anatabine, a minor alkaloid, is nitrosated to form N'-nitrosoanatabine (NAT). NAT constitutes approximately 40% of total TSNAs. The biosynthesis of anatabine, and its associated genes, is not completely known. However, current understanding is that the synthesis of anatabine requires quinolinate phosphoribosyltransferease (QPT), a key enzyme regulating entry to the pyridine nucleotide cycle.

Biosynthesis of anatabine is thought to proceed via the conversion of nicotinic acid to 3,6-dihydronicotinic acid. After decarboxylation to produce 3,6-dihydropyridine, and condensation with nicotinic acid to produce an intermediate, conversion to anatabine can occur by dehydrogenation. The current understanding of the alkaloid biosynthetic pathway is depicted in FIG. 1.

In addition to TSNAs, certain polyphenol compounds can form undesirable phenolic compounds during the combustion of tobacco and may also be targeted constituents of tobacco smoke. There is interest in providing a method for reducing the contents of these targeted compounds in tobacco.

BRIEF SUMMARY

The present disclosure significantly reduces and/or eliminates anatabine biosynthesis in tobacco. This prevents anatabine, a precursor of N'-nitrosoanatabine (NAT), from accumulating. NAT represents approximately 40% of total Tobacco Specific Nitrosamines (TSNAs), and as a result of elimination of anatabine as precursor, a 40% reduction in total TSNAs will be possible. This "ultra-low anatabine" trait can be combined with an ultra-low nornicotine trait in a tobacco line or variety to accomplish a further reduction of TSNA accumulation, as nornicotine is a precursor for N'-nitrosonornicotine formation. The combined ultra-low anatabine and ultra-low nornicotine traits could result in a reduction of total TSNAs on the order of about 70-80%.

The present disclosure details the development of an ultra-low anatabine trait through induced variation (EMS treatment) followed by a screen for plants deficient in anatabine. The ultra-low anatabine trait can be crossed into other commercial varieties, or the trait can be induced in a similar fashion directly into commercial tobacco varieties.

Currently there is no commercially relevant tobacco variety with reduced anatabine in leaf lamina. Since anatabine is a precursor for NAT which constitutes ~40% of total TSNAs, this trait has applicability in producing tobacco with very low TSNAs for tobacco products.

The ultra-low anatabine plants are also ideal genetic material for discovery of molecular markers that are closely linked with genes required for anatabine biosynthesis, as well as the actual discovery of genes required for anatabine biosynthesis. As disclosed, a method for discovery of molecular markers that are closely linked with genes required for anatabine biosynthesis may comprise crossing a reduced TSNA tobacco plant with another tobacco plant, isolating genomic DNA from individual progeny of the cross, and detecting in the genomic DNA the presence or absence of a molecular marker that is closely linked with a gene required for anatabine biosynthesis. Also as disclosed, a method for discovery of genes required for anatabine biosynthesis may comprise crossing a reduced TSNA tobacco plant with another tobacco plant, isolating genomic DNA from individual progeny of the cross, and detecting in the genomic DNA the presence or absence of a gene required for anatabine biosynthesis.

BRIEF DESCRIPTION OF THE DRAWINGS

FIG. 3 illustrates the percent anatabine content present in selected FC401 mutant lines at different generations.

FIG. 4 illustrates that the total anatabine content present in a selected TN90 LC mutant line at M2 and M3 generations.

DETAILED DESCRIPTION OF THE PREFERRED EMBODIMENTS

Figure 1:
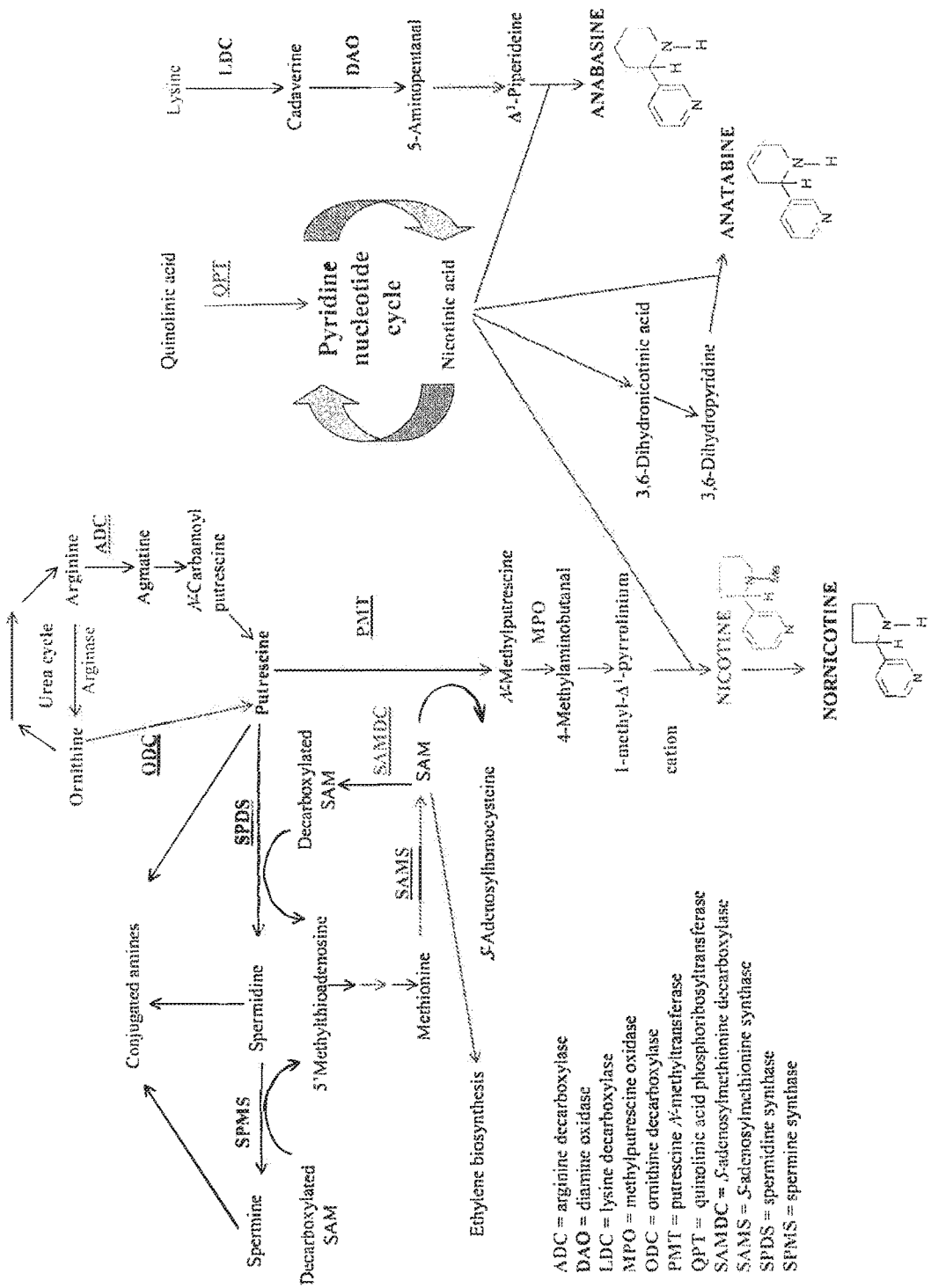
FIG. 1 depicts the alkaloid biosynthetic pathway.

As used herein, "tobacco material" denotes a tobacco starting material to be treated in various processes described herein, regardless of type, source or origin, which may have previously been subjected to other treatments. The tobacco material may include, but is not limited to, tobacco solids and any solid form of tobacco, such as, e.g., cured tobacco (such as flue-cured tobacco); uncured tobacco (also known as green tobacco); dried, aged, cut, ground, stripped or shredded tobacco; tobacco scrap; expanded tobacco; fermented tobacco; reconstituted tobacco; blended tobacco, etc. The tobacco material may be from any parts of the tobacco plant, such as leaf, stem, veins, scrap and waste tobacco, cuttings, etc.

In one embodiment, the smoking article is a cigarette.

Preferably, smokeless tobacco oral delivery products, such as chewing tobacco or pouched tobacco, are sized to comfortably be received in a human mouth. In addition, the oral products may be sized so that it can be moved around inside a human mouth.

A pouched tobacco typically contains an external wrapper and a tobacco material therein. The external wrapper preferably comprises a membrane that is sufficiently porous to allow passage through the membrane of a liquid, such as saliva, in the mouth. The external wrapper membrane is preferably resistant to deterioration in the presence of saliva and bacteria, and may be constructed from cellulose fiber such as tea bag material.

One embodiment provides a method of producing a reduced tobacco-specific nitrosamine (TSNA) tobacco plant comprising reducing and/or eliminating anatabine biosynthesis in wild-type tobacco plant. This may include preventing the accumulation of anatabine, the precursor of N'-nitrosoanatabine (NAT). This method may also comprise crossing said tobacco plant with reduced and/or eliminated anatabine biosynthesis with a tobacco plant having low nornicotine synthesis. A further embodiment is a reduced TSNA tobacco plant developed from these methods or a plant cell line produced from these methods. The TSNA levels can be reduced by at least about 40% when compared to a wild-type tobacco plant. Further envisioned is where the TSNA levels are reduced by at least about 70% when compared to a wild-type tobacco plant.

Another embodiment is the reduced TSNA tobacco plant in which a portion of said plant is used in a consumable tobacco product. This tobacco product can be, e.g., a cigarette or a smokeless tobacco product made from a reduced TSNA tobacco plant. Another embodiment is seeds from the reduced TSNA tobacco plant comprising reduced levels of anatabine.

Another embodiment provides a method for discovery of molecular markers that are closely linked with genes required for anatabine biosynthesis or discovery of genes required for anatabine biosynthesis comprising crossing a reduced tobacco-specific nitrosamine tobacco plant with another plant, isolating genomic DNA from individual progeny of the cross, and detecting in the genomic DNA the presence or absence of a molecular marker that is closely linked with a gene required for anatabine biosynthesis or a gene required for anatabine biosynthesis.

The embodiments disclosed herein are further illustrated by the following specific examples but is not limited hereto.

EXAMPLES

Example I

A novel genetic variation in a population of tobacco plants was created to identify plants that have lost the ability to biosynthesize anatabine. These plants are very likely to have a mutated non-functional version of one or more genes critical for anatabine biosynthesis. To induce novel genetic variation plants were treated with Ethyl methane sulfonate (EMS) and propagated to the M2 stage so that recessive mutations would express in plants homozygous for mutated genes.

A population of the Flue-cured variety "401" and TN90 was available for this investigation. Approximately 5000 seeds per variety were treated with 0.8% ethyl methane sulfonate and germinated. M1 plants were grown in the field and M2 seeds were collected. Approximately 2000 FC401 M2 and 500 TN90 M2 seeds were germinated and grown in 6" pots. At 50% flowering stage, plants were topped and leaf samples were collected after 2 weeks of topping.

Alkaloids were extracted from the leaf samples: 1 ml methanol per gram tissue was added and sonicated for 30 minutes. The extract was centrifuged briefly to pellet the residual leaf tissue and purified extract was concentrated 10 times by vacuum centrifugation for approximately 75 minutes at 45° C. Five microliters of concentrated sample along with standards were loaded on HPTLC plates. After samples were dried for 20 minutes, the plate was transferred quickly into the developing chamber saturated with a solvent mixture of Toluene: Ethyl acetate: Diethylamine (5:4:1 respectively). The plate was run for approximately 10-15 minutes until the mobile phase ran through approximately 75% of the length of the plate. The plate was air dried and photographed under UV254 using a documentation system with video (CAMAG REPRO STAR 3). This image is reproduced in FIG. 2.

Alkaloid Analysis: Tobacco leaves were harvested and air-dried in an oven at 50° C. A one gram sample of crushed, dried leaf was added to 10 mL of 2 N NaOH in an extraction bottle. The sample was mixed and allowed to incubate for 15 minutes at room temperature. Alkaloids were extracted by the addition of 50 mL of extraction solution [0.04% quinolone (wt/vol) dissolved in methyl-tert-butyl ether] and gently rotated on a linear shaker for 3 hours. Following phase separation, an aliquot of the organic phase was transferred to a sample vial. Samples were analyzed using an Agilent 6890 Gas Chromatograph and 5973N Mass Spectrometer.

Figure 2:
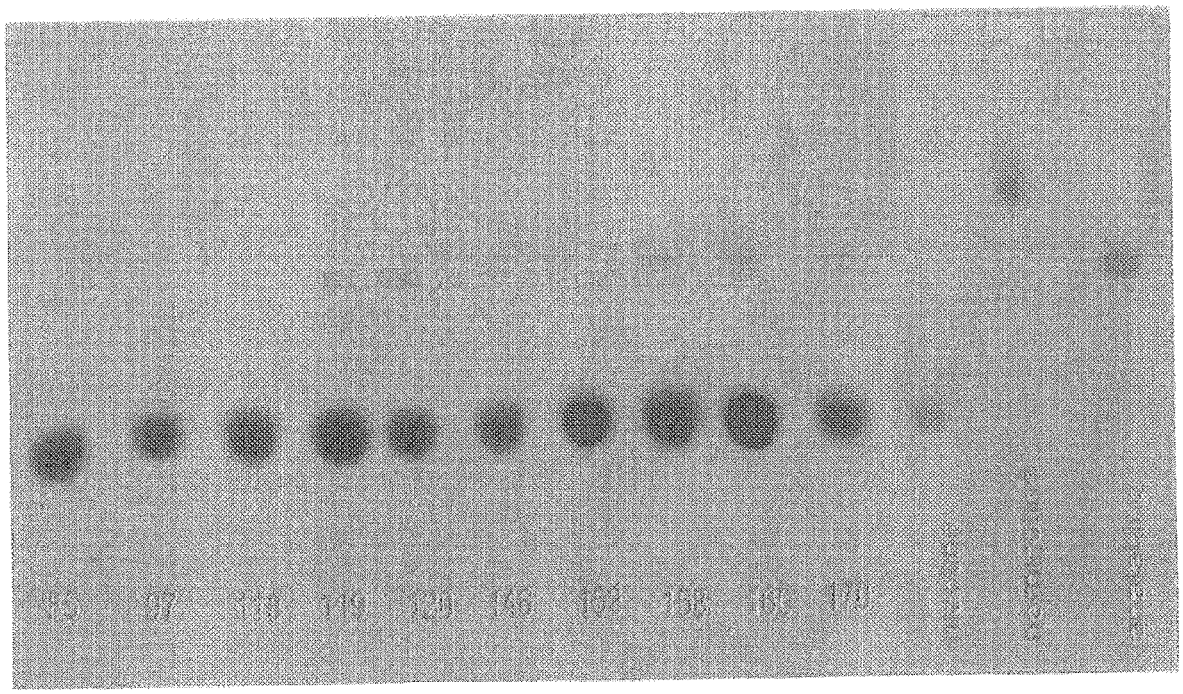
FIG. 2 shows the reduction of anatabine content compared to other mutant lines.

A total of 726 FC401 and 500 FN90 leaf samples were processed and screened for anatabine mutants. Mutant plants 97 (08GH97) and 153 (08GH153) in FIG. 2 show the reduction of anatabine content compared to other mutant lines. Using HPTLC screening and GCMS, 4 mutant lines were identified from FC401 and TN90 (Table 1). Mutants from dMS932 (ATCC® Accession Number PTA-124990), MF445 from FC401, and MS 3908 from TN90 mutant seeds were used for further analysis.

TSNA Analysis: Tobacco leaves were harvested and freeze-dried and powdered to 1 mm size. A 750 mg powdered sample was added to 30 mL of 100 mM ammonium acetate in a 60 mL amber vial. The sample was mixed and incubated in a shaker for 30 minutes. Approximately 4 mL of sample was transferred directly into labeled disposable culture tubes and 0.250 mL of concentrated ammonium hydroxide was added. The sample was vortexed for 1-5 seconds, after which time 1.5 mL of sample was added to a preconditioned extraction cartridge with a flow rate of 1-2 drops per second. Cartridges were washed and dried. Analytes from the extraction cartridges were eluted using 1.5 mL of 70:30 methanol:0.1% acetic acid and analyzed using liquid chromatography with tandem mass spectrometry (LC/MS/MS).

TABLE 1

Alkaloid Analysis by HPTLC and GC/MS

| Variety | Seed ID | Plant ID | Nicotine (%/g dry wt) | Nornicotine (%/g dry wt) | Anabasine (%/g dry wt) | Anatabine (%/g dry wt) | Total Alkaloids (%/g dry wt) | % Anatabine (%/g dry wt) |
|---|---|---|---|---|---|---|---|---|
| FC401 mutant 1 | MS108 (dMS932) | 08GH97 | 1.46 | 0.0412 | 0.00429 | 0.0115 | 1.517 | 0.76 |
| FC401 mutant 2 | MS445 | 08GH361 | 2.15 | 0.136 | 0.00423 | 0.0216 | 2.312 | 0.93 |

TABLE 1-continued

Alkaloid Analysis by HPTLC and GC/MS

| Variety | Seed ID | Plant ID | Nicotine (%/g dry wt) | Nornicotine (%/g dry wt) | Anabasine (%/g dry wt) | Anatabine (%/g dry wt) | Total Alkaloids (%/g dry wt) | % Anatabine (%/g dry wt) |
|---|---|---|---|---|---|---|---|---|
| FC 401 mutant 3 | MS170 | 08GH153 | 1.190 | 0.0224 | 0.00420 | 0.0084 | 2.312 | 0.93 |
| FC 401 | FC401 Control | 08GH1625 | 1.97 | 0.0476 | 0.0102 | 0.0875 | 2.115 | 4.41 |
| TN90 mutant 1 | MS3908 | 09MN8938 | 4.08 | 0.092 | 0.0047 | 0.021 | 4.198 | 0.51 |
| TN90 control | TN90 LC Control | 09N26 | 4.44 | 0.118 | 0.0129 | 0.123 | 4.694 | 2.62 |

FIG. 3 shows consistently low anatabine levels in mutagenized lines of the FC401 tobacco strain through multiple generations. Note that the data in M2 is from a single plant, while M3 and M4 are average values from multiple plants. FIG. 4 shows consistently low anatabine levels in a mutagenized line of the Tennessee Burley 90 (TN90) strain through multiple generations. As with FIG. 3, the data in M2 is from a single plant, while M3 is data of average values from multiple plants.

Figure 5:
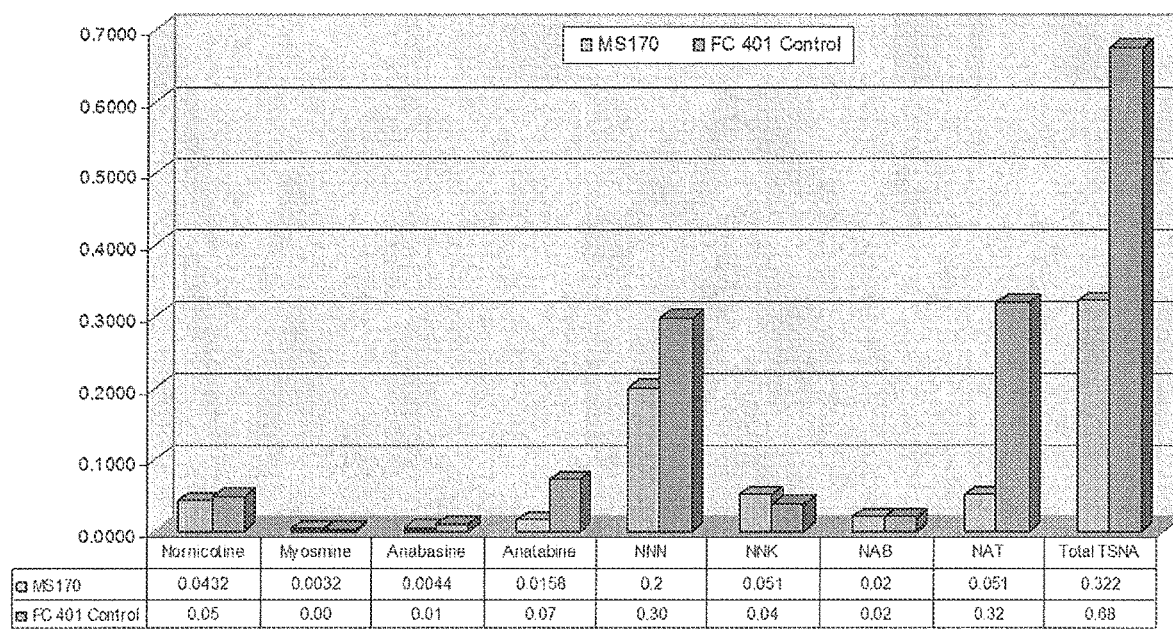
FIG. 5 illustrates that the low anatabine FC401 M2 mutant line shows reduced NAT.

FIG. 5 shows the result of 750 M2 plants screened using High Performance Thin Layer Chromatography (HPTLC). 12 plants were selected during initial screening and mutants containing the least anatabine are presented. Control plants: Total alkaloid content in FC401 is 2-3%; percent anatabine is 2.5-3% and NAT ranges from 0.2-0.4 PPM. Anatabine mutant: Total alkaloid content 3.16%; percent anatabine 0.5% and NAT is 0.051%. i.e~over 80 percent reduction.

While the foregoing has been described in detail with reference to specific embodiments thereof, it will be apparent to one skilled in the art that various changes and modifications may be made, and equivalents thereof employed, without departing from the scope of the claims.

All of the above-mentioned references are herein incorporated by reference in their entirety to the same extent as if each individual reference was specifically and individually indicated to be incorporated herein by reference in its entirety.

Deposit Information: A deposit of the proprietary *Nicotiana tabacum* dMS932 line disclosed above and recited in the appended claims has been made with American Type Culture Collection (ATCC®), 10801 University Boulevard, Manassas, VA 20110, USA. The date of deposit for *N. tabacum* line dMS932 was Feb. 21, 2018. The deposit of 100 packets each containing 25 seeds (2500 total seeds) was taken from the same deposits maintained since prior to the filing date of this application. Upon issuance of a patent, all restrictions upon the deposits will be irrevocably removed, and the deposits are intended by Applicant to meet all of the requirements of 37 C.F.R. §§ 1.801-1.809. ATCC® has issued the accession number: ATCC® Accession No. PTA-124990 for this deposit of *N. tabacum* line dMS932. This deposit will be maintained in the depository for a period of 30 years, or 5 years after the last request, or for the effective life of the patent, whichever is longer, and will be replaced as necessary during that period. Applicant does not waive any infringement of their rights granted under this patent or under the Plant Variety Protection Act (7 U.S.C. 2321 et seq.)

What is claimed is:

1. A pouched tobacco product comprising tobacco material from a tobacco plant from tobacco plant line dMS932, wherein a representative sample of seed of said tobacco plant line is deposited under ATCC® Accession No. PTA-124990.

2. The pouched tobacco product of claim 1, wherein the pouched tobacco product is sized to be received in a human mouth.

3. The pouched tobacco product of claim 1, wherein the pouched tobacco product is sized to be moved around inside a human mouth.

4. The pouched tobacco product of claim 1, wherein the pouched tobacco product contains an external wrapper and the tobacco material therein.

5. The pouched tobacco product of claim 4, wherein the external wrapper comprises a membrane.

6. The pouched tobacco product of claim 5, wherein the membrane is sufficiently porous to allow passage of a liquid through the membrane.

7. The pouched tobacco product of claim 6, wherein the liquid is saliva.

8. The pouched tobacco product of claim 5, wherein the membrane is resistant to deterioration in the presence of saliva.

9. The pouched tobacco product of claim 5, wherein the membrane is resistant to deterioration in the presence of bacteria.

10. The pouched tobacco product of claim 5, wherein the membrane is constructed from cellulose fiber.

11. The pouched tobacco product of claim 1, wherein the tobacco material is cured tobacco material.

12. The pouched tobacco product of claim 11, wherein the cured tobacco material is flue-cured tobacco material.

13. The pouched tobacco product of claim 1, wherein the tobacco material is selected from the group consisting of uncured tobacco material, dried tobacco material, and aged tobacco material.

14. The pouched tobacco product of claim 1, wherein the tobacco material is selected from the group consisting of ground tobacco material, stripped tobacco material, and shredded tobacco material.

15. The pouched tobacco product of claim 1, wherein the tobacco material comprises material from tobacco leaf.

16. The pouched tobacco product of claim 1, wherein the tobacco material comprises material from tobacco stem.

* * * * *